US00PP09037P

United States Patent [19]

Delbard

[11] Patent Number: Plant 9,037

[45] Date of Patent: Jan. 10, 1995

[54] HYBRID TEA ROSE PLANT NAMED DELSTROBLA

[75] Inventor: Georges Delbard, Commentry, France

[73] Assignee: Société Civile Agricole Pépinières et Roseraies Georges Delbard, Commentry, France

[21] Appl. No.: 144,873

[22] Filed: Oct. 26, 1993

[30] Foreign Application Priority Data

Dec. 21, 1992 [FR] France ..... 12040

[51] Int. Cl.[6] ..... A01H 5/00

[52] U.S. Cl. ..... Plt./11

[58] Field of Search ..... Plt. 11, 12, 13

*Primary Examiner*—Howard J. Locker

*Attorney, Agent, or Firm*—Burns, Doane, Swecker & Mathis

[57] ABSTRACT

A new and distinct variety of Hybrid Tea rose plant is provided that abundantly forms attractive double flowers which are red striped with light pink and white. Such flowers are long lasting and comprise petals that detach cleanly. The plant exhibits a bushy growth habit, forms semi-vigorous to vigorous vegetation, and is well suited for greenhouse forcing for cut flower production. Additionally, the plant is very resistant to diseases when grown under greenhouse conditions and in the garden.

1 Drawing Sheet

SUMMARY OF THE INVENTION

The new variety of Hybrid Tea rose plant was created by artificial pollination wherein two parents were crossed which previously had been studied in the hope that they would contribute the desired characteristics. The female parent (i.e., the seed parent) of the new variety resulted from the crossing of the Lara variety (U.S. Plant Pat. No. 3,011) with the Candia variety (Non-patented in the U.S.). The male parent (i.e., the pollen parent) resulted from the crossing of the aromaepi variety (Non-patented in the U.S.) with the Korpek variety (Non-patented in the U.S.). The parentage of the new variety can be summarized as follows:

(Lara×Candia)×(Aromaepi×Korpek).

The seeds resulting from the above pollination were sown and 270 small plantlets were obtained which were physically and biologically different from each other. Selective study resulted in the identification of a single plant of the new variety.

It was found that the new variety of the present invention can be characterized by the following combination of characteristics:

(a) from a physical point of view it forms green mature wood, assumes a bushy growth habit, and forms attractive long-lasting red striped with light pink and white double flowers having consistent petals that detach cleanly, and (b) from the biological point of view it forms semi-vigorous to vigorous vegetation, produces flowers in abundance, exhibits the ability readily to be forced, and is very resistant to diseases when grown under greenhouse conditions and in the garden.

The new variety well meets the needs of the horticultural industry and is particularly well suited for growing in the greenhouse for the production of attractive long-lasting cut flowers that are red striped with light pink and white.

The new variety can be readily distinguished from other varieties in view of the combination of characteristics described herein. It exhibits long and relatively straight stems, rigid and substantially straight peduncles, an excellent ability to be forced under greenhouse conditions, and a long vase life for its distinctive red striped blooms.

The new variety has been found to undergo asexual propagation and can be readily reproduced by conventional routes, such as budding (i.e., eye grafting). This asexual reproduction as performed at Hyères, France by budding, cuttings, and tissue culture has demonstrated that the characteristics of the new variety are strictly transmissible from one generation to another and are firmly fixed.

The new variety has been named the Delstrobla variety.

BRIEF DESCRIPTION OF THE PHOTOGRAPH

The accompanying photograph shows as nearly true as it is reasonably possible to make the same in a color illustration of this character typical specimens of the plant parts of the new variety. The rose plants of the new variety were grown under glass at Hyères (Var), France.

FIG. 1 illustrates a specimen of a young shoot;

FIG. 2 illustrates a specimen of a floral bud at the opening of the sepals;

FIG. 3 illustrates a specimen of a floral bud at the opening of the petals;

FIG. 4 illustrates a specimen of a flower in the course of opening;

FIG. 5 illustrates a specimen of an open flower in a more advanced stage of opening;

FIG. 6 illustrates a specimen of an open flower — plan view — obverse;

FIG. 7 illustrates a specimen of another fully open flower — plan view — obverse;

FIG. 8 illustrates a specimen of a fully open flower — plan view — reverse;

FIG. 9 illustrates a specimen of a fully open flower — plan view — obverse;

FIG. 10 illustrates a specimen of a floral receptacle showing the arrangement of the stamens and pitals;

FIG. 11 illustrates a specimen of a floral receptacle showing the arrangement of the pistils (sepals and stamens removed);

FIG. 12 illustrates a specimen of a main branch;

FIG. 13 illustrates a specimen of a flowering stem;

FIG. 14 illustrates a specimen of a leaf with three leaflets — plan view — upper surface;

FIG. 15 illustrates a specimen of a leaf with five leaflets — plan view — upper surface;

FIG. 16 illustrates a specimen of a leaf with five leaflets — plan view — under surface; and FIG. 17 illustrates a specimen of a leaf with seven leaflets — plan view — upper surface.

DETAILED DESCRIPTION

The chart used in the identification of the colors is that of The Royal Horticultural Society (R.H.S. Colour Chart). The description is based on the observation of plants grown under glass at Hyères (Var), France. The coloration in common terms sometimes also is provided.

Class: Hydrid Tea.

Plant:

*Height.*—Plants which were pruned to a height of 1 m. produce floral stems having a length of approximately 40 to 70 cm., and an average length of approximately 55 cm.

*Habit.*—Bushy.

Branches:

*Color.*—Young shoots: when approximately 20 cm. long, exhibit a green coloration, Yellow-Green Group 146B and 146C, commonly with a shaded bronze coloration on one side. Floral stems: Yellow-Green Group 146B. Mature wood: Yellow-Green Group 146A.

*Thorns.*—Configuration concave on the upper and under edges. Quantity: few which are 5 mm. or less in length, and the majority are greater than 5 mm. in length. The prickles are long and sharp, and the quantity of the prickles is normal for the class. Length: approximately 9 mm. on average on floral stems and approximately 9 mm. on average on mature wood, and commonly range in length from approximately 1 to 14 mm. in both instances. Color: on shoots of approximately 20 cm. in length they are reddish at the base and Yellow-Green Group 146C at the tip; on floral stems they are Yellow-Green Group 152D at the base with bronze coloration at the tip; and on mature wood they are slightly darker than Greyed-Orange Group 165B.

*Leaves.*—Number: typical for the class. Size: medium, typical for the class. Serration: present, single but not necessarily regular. The serration is not regular in the sense that each ridge is necessarily of the same size. General appearance: consistent, and medium in glossiness. Stipules: adnate, medium in size, and normal for the class. Petiole: the inner surface is grooved with non-glandular edges; and the outer surface may bear from 0 to 5 very small hooked prickles of 1 to 2 mm. in length. Petiole color on young shoot: Greyed-Purple Group 187A on upper surface and Yellow-Green Group 146B and 146C on under surface. Petiole color on floral stem: Yellow-Green Group 146A on upper surface and Yellow-Green Group 146B on surface. Petiole color on mature wood: Yellow-Green Group 146A on upper surface and Yellow-Green Group 146B on under surface. Petiole length of terminal leaflet: approximately 0.5 to 20 mm., approximately 10 mm. on average, with a standard deviation of 0.3 mm. Terminal leaflet length: approximately 36 to 86 mm., approximately 56 mm. on average, with a standard deviation of 0.5 mm. Terminal leaflet width: approximately 21 to 47 mm., approximately 34 mm. on average, with a standard deviation of 0.7 mm. Terminal leaflet shape at base: obtuse to rounded. Leaflet cross section: convex. Leaflet color of young shoot: Greyed-Purple Group 187A and 187B with bronze coloration at the margin and green coloration towards the middle of the leaflet on upper surface, and Greyed-Purple group 187B turning to bronze with green coloration on under surface. Leaflet color on floral stem: Yellow-Green Group 147A on the upper surface and Yellow-Green Group 146A and 146B on the under surface. Leaflet color of mature wood: Yellow-Green Group 147A on upper surface and Yellow-Green Group 146B on under surface.

Inflorescence:

*Number of flowers.*—Generally one per stem when grown under forced greenhouse conditions; however, sometimes in such forced culture the first axillary eyes below the flower develop and form approximately 3 to 5 flowers; and when grown outside in the landscape multiple flowers which number approximately 1 to 5 are produced in regular clusters.

*Peduncle.*—Erect, stiff, Yellow-Green Group 144A in coloration when the petals open, and commonly approximately 56 to 106 mm. in length (approximately 77 mm. on average). On the peduncle of the flower there are some prickles. Usually their length is <2.5 mm, but in a few exceptional instances they can reach 4 mm in length.

*Sepals.*—Configuration: absent to weak extensions. Commonly the sepals are 28 to 36 mm. in length. Under greenhouse conditions one sepal may assume a longer length of approximately 64 mm. Commonly 4 sepals are approximately 9 mm. in width. Under greenhouse conditions one sepal may assume a greater width of approximately 18 mm. Color: Yellow-Green Group 147C on the upper surface, and Yellow-Green Group 144A on the under surface.

*Buds.*—Shape: ovate in longitudinal section just before the opening of the sepals. Size before calyx breaks: the bud lenghts are commonly are approximately 20 to 23 mm., with an average of approximately 21 mm. Color: on the outside as the calyx breaks, Red Group 53C and 53D, striped with pink, Red Group 55B to 55D, and white.

*Flower.*—Time: early flowering. Shape: double. Form: round when viewed from above, and flattened convex when viewed from the side. Diameter: medium to large, approximately 8.5 to 11 cm., and approximately 9.5 cm. on average, with a standard deviation of 1 cm. Petal number: commonly approximately 40 to 52, and an average of approximately 44. Petal size (second row from outside: the length is approximately 43 to 56 mm. with a mean of approximately 46 mm., and a standard deviation of 0.3 mm.; and the width is approximately 40 to 55 mm. with a mean of approximately 47 mm., and a standard deviation of 0.4 mm. Petal shape: the first row of petals commonly exhibit a broad ovate configuration, the undulation of the petal margin is average, and the reflexing of the margin is average. Petal color: This description of an open flower was made during June while observing a flower that had been undergoing opening for 3 days. Petal color (middle zone): on the inner surface Red-Purple Group 58B striped with light pink Red Group 55B and 55C, and nearly white; and on the outer surface Red-Purple Group 58C striped with light pink, Red Group 55D, and with nearly white. Petal color (marginal zone): on the inner surface Red-Purple Group 58B striped with light pink, Red Group 55B and 55C, nearly white in some places, and on the outer surface Red-Purple Group 58C striped with light pink, Red Group 55D, and with nearly white. Petal spot at base: very small. Color of spot inner side: Yellow Group 4B and 4C. Color of spot outer side: Yellow Group 4C and 4D. Stamens: approximately 42 in number and are somewhat regularly arranged around the pistils. Filaments: most with an anther, medium in length and Yellow Group 13C with reddish coloration. Anthers: medium in size, each opens at approximately the same time, and the immature coloration is Yellow-Orange Group 22A and 22B. Pollen: the quantity of the pollen grains is few and they are Yellow-Orange Group 21A in coloration. Pistils: approximately 60 in number. Styles: medium in length and Red-Purple 61C in coloration. Stigmas: Yellow-Orange Group 14C at the tip and Red-Purple Group 61C at the base, and generally are present at approximately the same level as the anthers, but a few anthers may be higher. Hips: in longitudinal section they are in the shape of a pitcher, and approximately 22 mm. in diameter. Seeds: medium in size, approximately 20 to 25 in number, and average approximately 23 in number. Petal drop: petals detach cleanly. Fragrance: slight. Lasting quality: long.

Development: The blossoms commonly last approximately 8 days on average in a vase, and commonly last approximately 3 to 8 days on average on the plant depending upon the temperature and the season of the year.

*Vegetation.*—Semi-vigorous to vigorous.

*Blooming.*—Very abundant and almost continuous.

*Resistance to forcing.*—Excellent.

*Resistance to diseases.*—Very good under greenhouse conditions, and also when grown outside. Normally when grown outside this variety does not manifest symptoms of powdery mildew, and only a few leaves commonly will manifest the symptoms of black spot particularly at the end of the growing period (e.g., August/September). This resistance to diseases was characterized at a test site located at Hyères, France, where plants are sprayed three times during the growing season. The reported results are considered to be highly satisfactory under these conditions.

I claim:

1. A new and distinct variety of Hybrid Tea rose plant characterized by the following combination of characteristics:

(a) from a physical point of view it forms green mature wood, assumes a bushy growth habit, and forms attractive long-lasting red striped with light pink and white double flowers having consistent petals that detach cleanly, and (b) from the biological point of view forms semi-vigorous to vigorous vegetation, produces flowers in abundance, exhibits the ability readily to be forced, and is very resistant to diseases when grown under greenhouse conditions and in the garden;

substantially as herein shown and described.

* * * * *

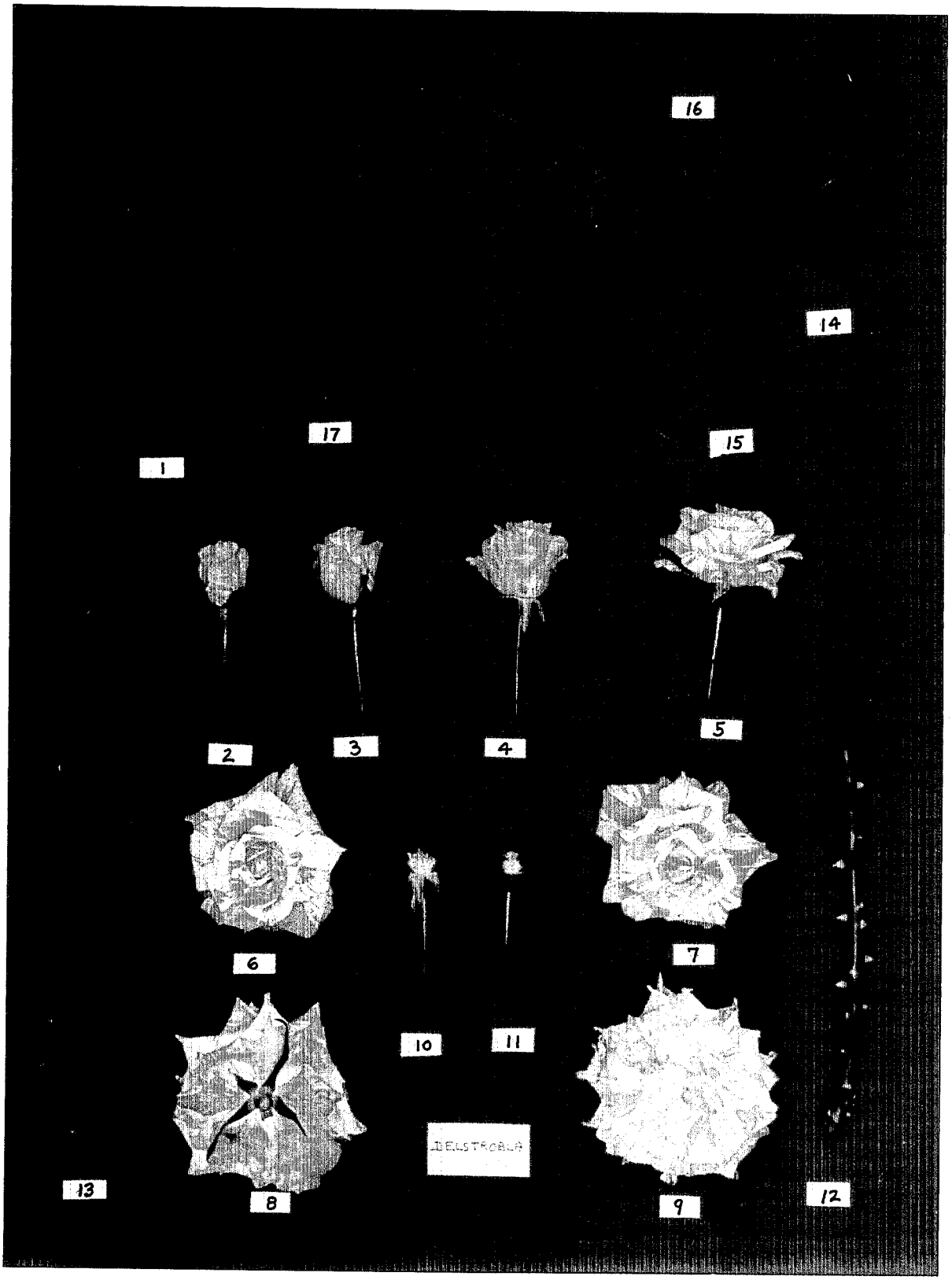
16
14
17
15
1
2
3
4
5
6
7
10
11
IDELSTROBLA
13
8
9
12